United States Patent
Ollivier et al.

[11] Patent Number: 5,902,330
[45] Date of Patent: May 11, 1999

[54] LEAD FOR AN IMPLANTABLE MEDICAL DEVICE USING GLUE EXPANSION CHAMBER AND CANALS

[75] Inventors: Jean-Francois Ollivier, Guyancourt; Frederic Bessoule, Epinay S/orge; Bernard Demorgny, Montrouge, all of France

[73] Assignee: ELA Medical S.A., Montrouge, France

[21] Appl. No.: 08/895,735

[22] Filed: Jul. 17, 1997

[30] Foreign Application Priority Data

Jul. 19, 1996 [FR] France .................................. 96 09068

[51] Int. Cl.⁶ ..................................................... A61N 1/05
[52] U.S. Cl. ........................................... 607/122; 607/116
[58] Field of Search .................................. 607/122, 126, 607/128, 116

[56] References Cited

U.S. PATENT DOCUMENTS

| | | | |
|---|---|---|---|
| 4,566,467 | 1/1986 | DeHaan | 128/784 |
| 4,917,106 | 4/1990 | Olivier | 128/785 |
| 5,016,646 | 5/1991 | Gotthardt et al. | 607/122 |
| 5,029,585 | 7/1991 | Lieber et al. . | |
| 5,231,996 | 8/1993 | Bardy et al. | 128/785 |
| 5,259,394 | 11/1993 | Bens . | |

FOREIGN PATENT DOCUMENTS

| | | | |
|---|---|---|---|
| 0 191 238 | 8/1986 | European Pat. Off. | A61N 1/05 |
| 2 616 072 | 12/1988 | France | A61N 1/05 |
| WO 91/19533 | 12/1991 | WIPO | A61N 1/05 |

*Primary Examiner*—William E. Kamm
*Assistant Examiner*—Carl H. Layno
*Attorney, Agent, or Firm*—Orrick, Herrington & Sutcliffe LLP

[57] ABSTRACT

A lead for an implanted medical device, particularly for a cardiac pacemaker, which has at its extremity distal a hollow cylindrical body (10) presenting at its distal side an opening (22) receiving a stimulation electrode (16) which is mounted axially in this opening, the body and electrode being mechanically fixed and set together by gluing the wall of the body to the wall of the electrode. The internal wall of the body is conformed in a manner to provide between the electrode and body, when the electrode is mounted in the body, a peripheral space defining a chamber (30, 34) between the opposing walls (50, 52) of the body and the electrode. This chamber is a glue expansion chamber essentially closed as compared to the exterior except for an injection canal (32) and an escape canal (36). The injection and escape canals are oriented radially and open in the chamber at two distinct extremities of the chamber such that the chamber could be gradually filled by penetration of glue under pressure by the injection canal and the excess glue escapes by the escape canal once the chamber is filled with glue.

14 Claims, 1 Drawing Sheet

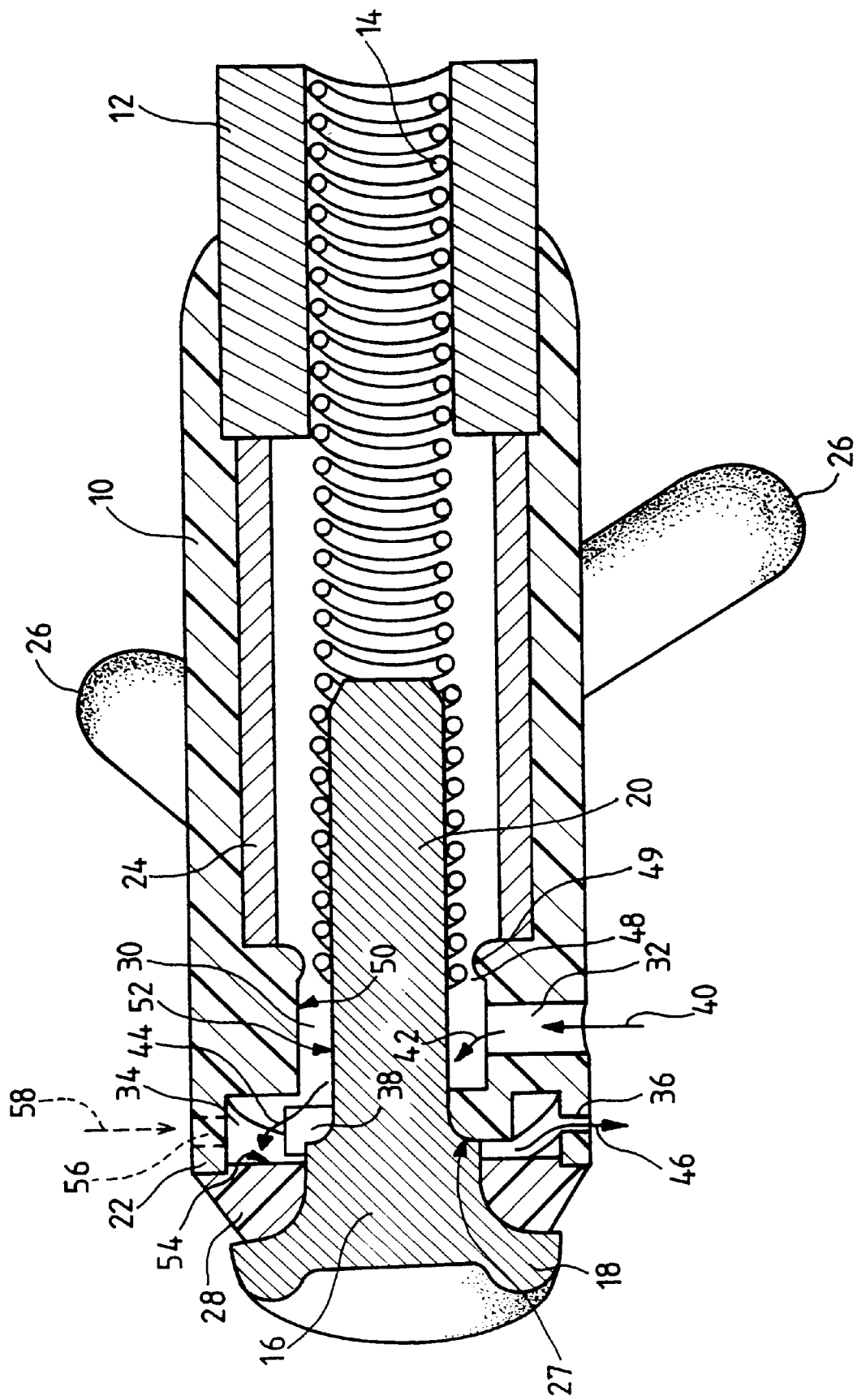

LEAD FOR AN IMPLANTABLE MEDICAL DEVICE USING GLUE EXPANSION CHAMBER AND CANALS

FIELD OF THE INVENTION

The present invention concerns the manufacture of leads for implanted medical devices, more particularly, cardiac stimulation leads.

BACKGROUND OF INVENTION

Typically, leads for implanted medical devices, such as, but is not limited to, cardiac stimulation devices, comprise an insulated sheath made of a flexible material having at least one internal electrical conductor (two conductors in the case of a bipolar lead), terminated at its distal extremity by an electrode disposed to contact tissue, for example, the wall of the myocardium in the case of a cardiac stimulation device.

The construction of the distal extremity of the lead is primarily an assembly of three elements, namely the cylindrical body (also known as "heart-side"), the stimulating electrode, and the internal conductor. The stimulation electrode is generally a porous carbon material that has the general form of a nail, with a head (stimulation surface in contact with the tissue) and an axial stem that is designed to allow connection to the internal conductor in the cylindrical body. The axial stem is typically cylindrical, although it also may be tapered. The head may be flat, convex or concave.

The internal conductor is a metallic element that is typically spiral wound inside the lead sheath. The mechanical and electrical connection between the electrode and the conductor is obtained by introducing, with force, the stem of the electrode into the spiral of the conductor, and alternately, according to a technique described in FR-A-2,616,072 and its corresponding U.S. Pat. No. 4,917,106, commonly assigned to the assignee hereof, ELA Medical, which U.S. Pat. No. 4,917,106 is incorporated herein by reference in its entirety.

The electrode and conductor are so fixed together, and the mechanical connection of the electrode to the cylindrical body is set by gluing, that is, by depositing a certain quantity of glue in an opening of the cylindrical body and by introducing into this cylindrical body opening the stem of the electrode, until the glue comes to overflow slightly in the periphery of the opening.

The technique of setting by gluing necessitates, however, a certain skill to master well the quantity of glue introduced, and to avoid particularly an overflow, especially on the active surface of the porous carbon electrode, which active surface has to be defined with precision because it is the surface electrode that fixes the polarization for the stimulation of the myocardium in the example described.

Although it is possible, in case of overflow, to wipe off the surplus of glue, the overflow can have already altered the active surface of the porous carbon electrode. Indeed, if the surplus of glue is not correctly cleaned, it is necessary, once the glue is hardened, to scratch (scrape) the surface of the electrode at this location in order to remove the glue and expose the material of the electrode. This can alter the qualities of this functional surface. During the injection of the glue, skill also is required because one also should also avoid the formation of bubbles in the glue, which bubbles could result in a bad fixation and/or a poor tightness of the connection between the electrode and the cylindrical body.

These difficulties are further complicated in the particular case of leads comprising, between the electrode and cylindrical body, a intermediary ring formed of a porous material containing an active material such as a steroid or other drug destined to be gradually distributed (or diffused) in the region of contact between the electrode and the myocardium. Here again, an overflow of glue on the functional surface of the diffusion ring creates a risk of reducing the surface available for releasing the active material, and therefore to modify the functional properties of the ring.

OBJECTS AND SUMMARY OF THE INVENTION

It is an object of the present invention to propose a lead structure allowing one to control better the distribution of the glue at the time the glue is injected and to avoid the aforementioned disadvantages, particularly by avoiding the risk of glue overflow on functional surfaces (or at least to limit the overflow to a very localized region, which is in any case non functional). By preserving the integrity of the functional surfaces of the porous carbon electrode and, where applicable, the diffusion ring of an active material, one controls more accurately, if not perfectly, the different parameters of the lead, and achieves an excellent reproducibility of the lead in terms of its design performance.

Furthermore, the disposition of the various elements described hereafter contributes to an improved dissociation of the function of stimulation and the function of diffusion of the medicinal substance in the case of a lead with such an active material.

To this end, the lead is of the known type, comprising at its distal extremity, a hollow cylindrical body presenting at its distal side an opening for receiving a stimulation electrode to be situated in the opening, preferably axially, the body and the electrode being mechanically fixed together and set by gluing the internal wall of the body to the body of the electrode. In accordance with the present invention, the internal wall of the body is conformed in a manner such that between the electrode and the body, when the electrode is mounted in the body, there is a peripheral space defining a chamber between the walls of the body and the walls of the electrode. This chamber is referred to as a glue expansion chamber, which is essentially closed to the exterior except for an injection canal and an escape canal. The injection and escape canals are preferably oriented radially, and open into the chamber at two distinct extremities of the chamber in a such manner that, as glue is injected into the chamber under pressure through the injection canal, the chamber is gradually filled with glue and, once the chamber is filled with glue, excess glue exits through the escape canal.

Preferably, the electrode inserted into the body also is electrically fixed to the internal conductor of the body, such that setting by the gluing also maintains the conductor electrically connected to the electrode.

In a first embodiment, the glue expansion chamber is an annular chamber defined by the interior wall of the cylindrical body and the exterior of a portion of the stem of the electrode. The injection and escape canals open in this chamber at diametrically opposite sites.

In a second embodiment, the glue expansion chamber has two distinct annular chambers connected therebetween by an internal transition canal, the injection canal opening into one of the two annular chambers and the escape canal opening in the other annular chamber, and the transition canal opening in each of chambers at a point diametrically opposite to the outlet of the injection and escape canals, respectively. This second implementation is advantageously applied in the case that it is foreseen that between the electrode and the body of the lead there is an intermediary ring having an internal face which defines an internal wall of one of annular chambers, in a manner such as to maintain also this ring fixed to the electrode and/or to the body by injection of glue in the glue expansion chamber. Such a ring could be a diffusion ring.

BRIEF DESCRIPTION OF THE DRAWING

Other characteristics and advantages of the present invention will appear to a person of ordinary skill in the art in view of the following description made with reference to the annexed drawing, which is a perspective sectional view of a distal extremity of a lead according to a preferred embodiment of the invention.

DETAILED DESCRIPTION OF THE DRAWING

With reference to the drawing figure, the reference 10 designates a hollow cylindrical body forming the distal extremity of the lead, and mounted to the extremity of a insulated flexible sheath 12 enclosing a metallic flexible spiral conductor 14 (it being understood that there are two such conductors in the case of a bipolar lead).

The cylindrical body 10, just as the insulated sheath 12, are generally made of a bio-compatible material such as a silicone resin.

The lead also comprises a stimulation electrode 16, typically made of a porous carbon material, and configured with a flat frontal extremity or head 18 constituting the active surface that is to be placed in contact with the wall of the myocardium. Head 18 extends from an axial stem 20 that extends inside the hollow cylindrical body 10. The conductor 14 is connected electrically and mechanically to the stem 20 by being introduced with a force (i.e., a frictional force fit) in the spiral of conductor 14, to obtain a sought-after contact by radial squeezing on the stem 20.

The cylindrical body 10 comprises at its distal extremity an opening 22 in which is lodged the electrode 16, centered by a shoulder 27. The body 10 also possesses an element 24 serving as a radio-opaque ring made of a rigid material having a cylindrical form, as well as conventional anchorage tines 26, which are destined to become inserted in the trabecula of the myocardium at the moment of the implantation of the lead.

In the illustrated example of a lead for a cardiac stimulation device, the lead also is equipped with a diffusion ring 28 placed around the electrode 16, between the head 18 and the outlet 22 of the cylindrical body. Ring 28 is generally constructed of a porous silicone loaded with an active material, such as a steroid or other drug or medicinal substance destined to be distributed (typically by diffusion out of a suitable support material or matrix) in the region of the myocardium in the vicinity of the electrode, so as to improve the performance of the lead after the implantation. Ring 28 is thus also referred to as a "diffusing ring" or a "drug eluting ring".

The manufacturing process of such a lead includes, as one has indicated above, fixing together the cylindrical body 10, the electrode 16 (that has been beforehand connected to the conductor 14) and the diffusion ring 28, if such a ring 28 is to be used. The fixation is set by gluing, and the gluing has to be uniform and tight, and especially without any overflow of glue on the functional surfaces of the electrode (that is, head 18) and the diffusing ring 28 (that is, the exposed external surface of the diffusing ring 28).

According to the invention, it is foreseen to conform inwardly the cavity of the cylindrical body 10 in a manner so as to provide, between the stem 20 of the electrode 16 and the cylindrical body 10, beyond (that is distally of) the conductor 14, a first annular chamber 30 completely surrounding the stem 20 of the electrode 16. This chamber 30 communicates with the exterior by an injection canal 32, which is preferably radially directed to chamber 30. It is expected also that there is a second annular chamber 34, positioned closer to the head 18 of the electrode than chamber 30, which communicates with the exterior by an escape canal 36, which escape canal 36 also may be radially directed. The two chambers 30 and 34 are thus isolated from each other except for a transition canal 38, for example, in the form of a radial opening realized in the shoulder 27 of the internal part of the cylindrical body 10. The injection canal 32 is situated diametrically opposite to the transition canal 38, that has, in turn, been situated diametrically opposite to the escape canal 36, in the case of the presence of a diffusing ring 28.

The glue, typically a conventional bio-compatible silicone glue, is injected through the use of a needle introduced into the injection canal 32. During the injection, the flow of glue is going to penetrate from the injection canal 32 (as indicated by arrow 40 in the drawing) and divide into two branches, one branch passing on each "side" of the stem 20 of the electrode (as indicated by arrow 42 of the drawing). The two branches (or fronts) of glue thus progress in the chamber 30 on both sides of the stem 20 and rejoin in the region of the transition canal 38. The rejoined branches then cross the transition canal 38 (arrow 44) and, again, separate into two branches (fronts) of glue, respectively advancing in the second chamber 34 on both sides of the stem 20. These latter two fronts advance along the shoulder 27, but in a position situated closer to the distal extremity than in chamber 30. The two fronts of glue then rejoin finally, after having made a tour around stem 20, in the vicinity of the escape canal 36, where the operator will see the excess glue exit (as indicated by arrow 46 of the drawing) and be able immediately to stop the further injection of glue.

It is at this point that, in accordance with the present invention, the operator is aware that the prescribed volume of glue has been well injected in the distal extremity of the lead, without bubbles or irregularities, and therefore with an excellent reproducibility of the gluing process, and without risk of alteration of the performance of the lead due to the absence of any glue overflow on functional surfaces of the electrode head 18 or on the diffusion ring 28.

The particular geometries of the two chambers 30 and 34, and of the injection canal 40, the transition canal 38, and the escape canal 36, combine to allow a continuous progression of the flow of glue throughout the totality of the cavity thus constituted, without formation of bubbles, with the escape canal 36 also playing the role of a vent during this gluing operation. Thus, filled, the glue is allowed to set or is cured in a conventional manner.

One thus controls thus in an improved manner the injected glue volume, according to precise dimensions of chambers 30 and 34, whose geometry is linked only to the desired or selected precision of manufacture of the cylindrical body 10 and the stimulation electrode 16. These chambers can be dimensioned in a manner so as to define precisely the thickness of the film of glue that will come in place in the space between surfaces 50 and 52, respectively of the cylindrical body 10 and the stem 20 of the electrode 16, as well as of the proximal surface 54 of the diffusion ring 28.

One will note that, in the proximal direction, a space 48 is situated between the end portion of the conductor 14 and the proximal portion of the cylindrical body 10. The space 48 is sufficiently small so as to prevent effectively any significant penetration of glue in the internal volume of the cylindrical body in the proximal direction, such that the flow of glue is essentially progressing in the chamber 30 and in the direction of the transition canal 38. In others terms, the flow resistance resulting from the volume of the chamber 30, the transition canal 38, the chamber 34 and of the escape canal 36 is much lower than the flow resistance formed by the space 48 between the extremity of the conductor 14 and the internal cavity of the cylindrical body 10. Space 48 in addition may be further reduced by the presence of an internal annular covering 49, reducing locally the diameter of the bore at the vicinity of the distal extremity of the conductor 14.

In a simplified variation of the invention, particularly for leads not comprising a diffusion ring 28, it is possible to construct a structure with a single chamber, the cylindrical body not comprising in this case the second chamber 34, and the injection canal being located at canal 56, diametrically opposite to the escape canal 36. The glue injection is then made (as indicated by arrow 58 in the drawing) by this injection canal 56, the glue coming to divide in two fronts that make the tour around the stem 20 of the electrode, to rejoin (as indicated by arrow 46 in the drawing) at the vicinity of the escape canal 36.

One skilled in the art will appreciate that the present invention can be practiced by other than the described embodiments, which are presented for purposes of illustration and not of limitation. For example, the distal lead portion of the present invention could be applied to tissue sensing or stimulation devices other than cardiac stimulation.

We claim:

1. A lead for an implanted medical device, comprising a distal extremity having a hollow cylindrical body having an internal wall (10) and presenting at a distal side an opening (22) receiving a stimulation electrode (16) mounted axially in this opening, the stimulation electrode having a wall, the body and electrode being mechanically fixed and set together by gluing the wall of the body with the wall of the electrode, said lead being characterized in that the internal wall of the body is conformed in a manner as to leave between the electrode and the body, when the electrode is mounted in the body, a peripheral space defining a chamber (30; 30, 34) between walls (50, 52) of the body and the electrode, this chamber comprising a glue expansion chamber essentially closed to the exterior except for an injection canal (32) and escape canal (36), said injection and escape canals being oriented radially and opening in the chamber in two distinct extremities of the chamber, in a manner so that said chamber could be gradually filled by penetration of glue under pressure at the injection canal and that the escape of the excess glue by the escape canal is realized once the filling is finished.

2. The lead of claim 1, in which the glue expansion chamber comprises an annular chamber (34) and said injection and escape canals open in this chamber at diametrically opposed sites.

3. The lead of claim 1, in which the glue expansion chamber comprises two distinct annular chambers (30, 34) connected therebetween by an internal transition canal (38), the injection canal opening in one of chambers and the escape canal opening in the other chamber, the transition canal opening in each of chambers at a site diametrically opposite to the outlet of the injection and of escape canals, respectively.

4. The lead of claim 3, further comprising a diffusion ring (28) between the electrode and the body, said diffusion ring having an internal face (54) defining an internal wall of one of annular chambers, in a manner so as to fix also said diffusion ring to the electrode and/or to the body by injection of glue in the glue expansion chamber.

5. A distal end of a lead for an implantable medical device comprising:

a hollow body having a distal opening and an interior surface;

a stimulation electrode having an exterior surface; and a glue expansion chamber;

wherein the stimulation electrode is mounted in said distal opening with said exterior surface opposite said body interior surface and said glue expansion chamber is defined by an annular space between said electrode exterior surface and said body interior surface, the glue expansion chamber further comprising an injection canal opening into said glue expansion chamber and an escape canal opening into said glue expansion chamber.

6. The lead distal end of claim 5 further comprising a glue, wherein said glue substantially fills said glue expansion chamber.

7. The lead distal end of claim 6 wherein the stimulation electrode further comprises a head and a stem, the stem comprising said exterior surface inserted in said body opening, and wherein the glue expansion chamber further comprises an annular space surrounding a portion of said stem exterior surface, wherein the injection canal and escape canal are radially directed relative to said annular chamber and diametrically opposed.

8. The lead distal end of claim 7 wherein the glue expansion chamber further comprises a first chamber, a second chamber and a transition canal connecting the first and second chambers, wherein the injection canal opens into one of the first and second chambers and the escape canal opens into the other of the first and second chambers, and transition canal is positioned opposite each of the injection canal and the escape canal.

9. The lead distal end of claim 8 further comprising a diffusion ring mounted at said body distal opening interposed between said electrode and said body, the ring having a surface area comprising a portion of one of the first and second chambers in contact with said glue.

10. The lead distal end of claim 8 wherein the electrode stem is axially mounted in said body and said first and second chambers each comprise an annular chamber.

11. The lead distal end of claim 8 further comprising an electrical conductor internal to said body in electrical contact with said electrode stem.

12. The lead distal end of claim 8 wherein the glue expansion chamber further comprises a distal end and a proximal end wherein the distal end is closed and the proximal end comprises a second annular space having a dimension that is smaller than the annular space.

13. The lead distal end of claim 7 further comprising an electrical conductor internal to said body in electrical contact with said electrode stem.

14. The lead distal end of claim 7 wherein the glue expansion chamber further comprises a distal end and a proximal end wherein the distal end is closed and the proximal end comprises a second annular space having a dimension that is smaller than the annular space.

* * * * *